(12) United States Patent
Pau et al.

(10) Patent No.: US 8,280,480 B2
(45) Date of Patent: Oct. 2, 2012

(54) STAPEDIUS MUSCLE ELECTRODE

(75) Inventors: Hans Wilhelm Pau, Rostock (DE); Detlef Behrend, Warnemünde (DE); Wolfram Schmidt, Rostock (DE); Klaus-Peter Schmitz, Warnemünde (DE)

(73) Assignee: Med-El Elektromedizinische Geraete GmbH, Innsbruck (AT)

( * ) Notice: Subject to any disclaimer, the term of this patent is extended or adjusted under 35 U.S.C. 154(b) by 376 days.

(21) Appl. No.: 12/527,263

(22) PCT Filed: Feb. 19, 2008

(86) PCT No.: PCT/EP2008/051995
§ 371 (c)(1),
(2), (4) Date: Feb. 16, 2010

(87) PCT Pub. No.: WO2008/101922
PCT Pub. Date: Aug. 28, 2008

(65) Prior Publication Data
US 2010/0145177 A1     Jun. 10, 2010

(30) Foreign Application Priority Data

Feb. 19, 2007  (DE) .................. 10 2007 008 154

(51) Int. Cl.
*A61B 5/04*  (2006.01)
(52) U.S. Cl. ....................... 600/379; 607/137
(58) Field of Classification Search .............. 600/379; 607/137
See application file for complete search history.

(56) References Cited

U.S. PATENT DOCUMENTS

| | | | | |
|---|---|---|---|---|
| 4,573,481 | A | 3/1986 | Bullara | 607/118 |
| 4,590,946 | A | 5/1986 | Loeb | 600/375 |
| 4,832,051 | A * | 5/1989 | Jarvik et al. | 607/116 |
| 6,205,360 | B1 | 3/2001 | Carter et al. | 607/57 |
| 6,208,882 | B1 | 3/2001 | Lenarz et al. | 607/137 |
| 2005/0216073 | A1 | 9/2005 | Jolly et al. | 607/137 |

* cited by examiner

*Primary Examiner* — Lee S Cohen
(74) *Attorney, Agent, or Firm* — Sunstein Kann Murphy & Timbers LLP

(57) ABSTRACT

The invention relates to a stapedius muscle electrode array for detecting the action elements generated when a human stapedius muscle is contracted. Said array comprises an electrode (2, 2', 2") that is adapted for bipolar discharge and is to be attached to a human stapedius muscle. The electrode has two flexible, elastic, electrically conducting elongate elements (2a, 2b), each of which has a distal (4a, 4b) and a proximal end (17a, 17b) and is helically preshaped along at least some of the length thereof to the distal end (4a, 4b) thereof in such a way that the distal end (4a, 4b) and a section of the respective elongate element (2a, 2b) which adjoins the distal end (4a, 4b) can be placed at least in part around the tendon (7) extending between the stapedius muscle and the stapes while the helical part can be guided along the tendon (7), can be moved in the direction of the stapedius muscle, and can be at least partly twisted into and/or slid onto the region of the muscle belly (6) adjoining the tendon (7). The two elongate elements (2a, 2b) are electrically insulated from one another, and the helical parts (3) thereof are intertwined in such a way as to run around a common centerline (11), allowing the helical parts (3) to be jointly placed around the tendon (7), be guided along the tendon (7), and be brought in contact with the stapedius muscle.

25 Claims, 3 Drawing Sheets

STAPEDIUS MUSCLE ELECTRODE

BACKGROUND OF THE INVENTION

The present invention relates to a stapedius muscle electrode for fastening on a human stapedius muscle and for detecting the action currents generated upon a contraction of the stapedius muscle.

The three auditory ossicles, the hammer, anvil, and stirrup, which cause the coupling of the eardrum to the inner ear, are located in the middle ear of a human. For this purpose, the hammer is connected to the inner side of the eardrum, while the stirrup is connected to the oval window of the inner ear. In this way, the hammer can absorb the vibrations of the eardrum and transmit them via the anvil, which is situated between the hammer and stirrup, and the stirrup to the oval window, whereby sound vibrations are generated in the liquid of the cochlea, which pass through the liquid. These sound vibrations set hair cells projecting into the liquid into movement, and the movement of the hair cells triggers nerve impulses, which are finally relayed to the brain to generate an impression of hearing.

Normally, it is desirable, as much as possible, for all of the sound power incident in the auditory canal to be relayed via the auditory ossicles to the inner ear. However, from a specific sound pressure, the undamped sound relay would result in damage to the inner ear. For this reason, a mechanism is provided in the human ear, using which the chain of the auditory ossicles can be influenced in their vibration behavior and the sound conduction provided thereby may be reduced in the event of strong acoustic events. This natural protective mechanism is based on two small muscles which involuntarily contract reflexively upon perception of a high sound level. The so-called tensor tympani muscle attaches on the hammer and tensions the eardrum, while the so-called stapedius muscle engages on the stirrup via a tendon associated therewith and tilts the base of the stirrup in the oval window. In this way, the chain of the auditory ossicles is stiffened, so that the coupling of the eardrum to the inner ear worsens. A part of the sound power incident on the eardrum is reflected on the eardrum and a further part is dissipated into the surrounding bone. The hearing is thus protected within certain limits from damage by excessively high sound pressures.

This reaction mechanism of the hearing to protect the inner ear from damage by excessively high sound levels, which results in the tensing of the stapedius muscle, is referred to as the stapedius reflex. It normally begins at sound levels of greater than approximately 80 to 100 dB and begins approximately 50 ms after the beginning of the sound exposure. The stapedius reflex is significant in medicine because conclusions about the functional capability of the ear may be drawn from an atypical behavior or its complete absence. Thus, the use of the reflex at relatively too low or relatively too high sound levels may indicate a functional disturbance of the ear, while its absence may indicate a loss of hearing related to the inner ear, for example, on the one hand, and a so-called otosclerosis—this is more significant from a clinical viewpoint—on the other hand, i.e., a sound conduction hearing impairment because of a fixation of the stirrup.

In addition, the observation of the occurrence of the stapedius reflex in connection with cochlear implants, which are used in deaf people whose deafness is caused by the absence or the destruction of the hair cells in the cochlea, is of great practical significance. This form of deafness cannot be overcome by conventional hearing aids, which only cause an amplification of the sound waves received by the ear. Rather, the electrical nerve impulses to be relayed to the brain must be artificially generated, which can be achieved by stimulation electrodes implanted in the cochlea, which form a part of the cochlear implant. The sense of hearing can often be at least partially reproduced by cochlear implants if the auditory nerve is intact in such a way that speech understanding is possible. However, it is important that the signal level output by the stimulation electrodes is set and regulated in a suitable way. Because the sound energy perceived by the patient can be concluded from the occurrence of the stapedius reflex, the measurement of the stapedius reflex may be used for the matching setting of the cochlear implant. If a sensor device for recognizing the stapedius reflex forms an integral part of the cochlear implant, self-adaptation of its energy output is possible.

To measure the stapedius reflex, inter alia, electrodes are used, which are brought into contact with the tissue of the stapedius muscle and in this way may pick up the action currents generated upon a contraction of the stapedius muscle and conduct them to a suitable measuring unit. However, the reliable contacting of the stapedius muscle has proven to be difficult, because the majority of it is situated inside a channel concealed in the bone and only a small part of it and its tendon are visible and readily accessible from the interior of the middle ear.

The publication U.S. Pat. No. 6,208,882 describes an array of differently designed electrodes for fastening on the stapedius muscle tissue.

One of these electrodes is formed by a serrated, flat blade, which is guided through a surgically produced (slot) incision in the stapedius muscle and held there by the serrations, which form barbs. This electrode has the disadvantage that the required incision in the muscle and the presence of barbs are connected to significant traumatization. In addition, because of the barbs it is only removable poorly and/or with complications. Alternatively, an electrode of this type may also be fastened in that a drilled hole is generated through the bones laterally delimiting the bony channel, and the blade is guided through the hole and bent upward in the channel, so that it runs between the inner wall of the channel and the stapedius muscle. For more secure fastening, the blade may additionally be bent over the upper edge of the channel. However, the disadvantage also exists in this case of traumatization because of the bone hole. In addition, there is an impedance increase in the remaining bone, and the blade is only controllable with difficulty during the fastening, so that the danger of direct traumatization of the muscle also exists.

Another of these electrodes comprises a biocompatible metal wire, which is flexible or pre-shaped in the form of a hook and which has a small ball on one end and is connected at the other end to a coiled insulated wire for connection to an analysis circuit. During the implantation, the electrode is inserted into the bony channel in such a way that the ball is pressed against the stapedius muscle and clamped between it and the adjoining bone. The correct positioning of this electrode requires special instruments. In addition, the hook shape is relatively bulky and the fastening is not very secure, so that the electrode may be easily dislocated by muscle movements. In addition, the removal of a piece of bone is sometimes necessary.

Further of these electrodes are implemented so that they may be laid around the section of the stapedius muscle protruding from the bony channel and secured. Thus, an electrode is formed by a silicone sleeve which can be clamped around the muscle, on whose inner side electrical contacts are implemented. Another electrode is formed by a hook-shaped or U-shaped pre-shaped wire, on whose ends small balls or loops are located and which may be bent and fixed around the stapedius muscle. These designs are not only complex to handle (e.g., they require a spreading instrument), and have relatively bulky and complex constructions, but rather their use also involves the danger of pressure necrosis.

Still another of these electrodes is formed by a multi-strand, Teflon-insulated platinum/iridium wire. For fastening in the muscle tissue, a piece of the insulation is removed on the front end of the wire and bent backward. Subsequently, a drilled hole is produced through the bone, through which the wire is inserted by a needle into the muscle belly. Upon removal of the needle, the bent-over wire front end acts as a hook which fixes the wire in the tissue. This is also disadvantageously connected to traumatization.

In general, these known stapedius muscle electrode configurations thus have the disadvantages that they are very traumatic, require drilled holes in bone, can only be implanted using special instruments, and/or have inadequate fixing upon muscle movements, and are difficult or impossible to remove again.

BRIEF SUMMARY OF THE INVENTION

It is the object of the present invention to provide a simply constructed stapedius muscle electrode configuration, which can be reliably fixed on the stapedius muscle without causing permanent damage and which overcomes the cited disadvantages.

The features of Claim 1 are used to achieve this object. Advantageous embodiments of the stapedius muscle electrode configuration are the subject matter of the associated subclaims.

According to the present invention, it is provided that a stapedius muscle electrode configuration comprises an electrode, which is adapted for bipolar derivation, for fastening on a human stapedius muscle, the electrode having two biocompatible, flexible, elastic, electrically conductive oblong elements, each of which has one distal end and one proximal end. In the present application, the term "proximal" typically means the end facing toward the operator during the fastening procedure, while the term "distal" typically relates to the end facing away from the operator and facing toward the patient. Accordingly, the distal end of the two oblong elements is the end which first comes into contact with the stapedius muscle during the correct electrode fastening described hereafter. Each of the two oblong elements is pre-shaped as coiled along its entire length or along a part of its length, the coiled part or section formed in this way extending up to the distal end of the oblong element in any case.

In the scope of the present application, "coiled" is understood as a course of an oblong element in which the oblong element coils around a linear, curved, or arbitrarily shaped imaginary line and simultaneously follows the direction of this line. The imaginary line which defines the general extension direction of the coiled course is referred to as the center line of the coiled course. In other words, the course is such that it at least partially encloses a volume whose cross-sectional area runs perpendicular to the general extension direction of the oblong element. The enclosed volume may have an arbitrary cross-sectional shape. An example of a coiled course is a spiral course.

The length and the radial coil diameter of the coiled part of the two oblong elements are selected so that the distal end and an area of the two oblong elements adjoining it are laid around the tendon running between the stapedius muscle and the stirrup and the coiled parts can be moved guided in the direction toward the stapedius muscle and at least partially screwed into the area of the muscle belly adjoining the tendon and/or pushed onto this area. The two oblong elements are electrically insulated from one another to allow a bipolar derivation through the electrode, however, no insulation being provided along a coiled section of each oblong element which may be brought into contact with a muscle belly by being pushed thereon, which could prevent an electrical contact with the muscle belly in this state. It is preferable if the two oblong elements are fastened to one another by an insulating material. In any case, the coiled parts of the two oblong elements are situated interleaved in one another so that they run around a shared center line and/or at least partially enclose a shared volume and may advantageously be laid together as a unit around the tendon, guided along the tendon, and brought into contact with the stapedius muscle. It is particularly advantageous if the coiled parts are implemented so that, by rotation around their shared center line (the two oblong elements rotating as a whole around the center line), they are moved in the direction toward the stapedius muscle guided along the tendon in a spiral as a unit and may be at least partially screwed into the area of the muscle belly adjoining the tendon and/or pushed onto this area.

The interleaved configuration of the two coiled parts of the two oblong elements having a shared center line means, in other words, that the coiled parts are entwined with one another and circle one another in coils. They are offset to one another along the center line so that, between the two turns of one or more pairs of adjacent turns of the coiled part of one of the two oblong elements, at least one turn of the coiled part of the other oblong element is located in each case, i.e., at least one turn of the other oblong element is located between at least two turns of one oblong element.

The laying of the distal tip and the area adjoining it of each oblong element around the tendon may be performed so that the tendon is only partially enclosed, or so that the tendon is completely enclosed. If the coiled part of an oblong element contains at least one complete turn, the oblong element initially preferably has its terminal turn completely laid around the tendon, i.e., the area of the oblong element adjoining the distal tip comprises at least the terminal turn in this case. In the event of multiple turns and the advantageous rotation around the center line, for example, one turn after another is "threaded" onto the tendon. If the coiled part of an oblong element contains less than one complete turn, the oblong element is laid around the tendon so that it only partially encloses it. In any case, because of the at least partially coiled course of the two oblong elements, in particular during the advantageous spiraling movement of the oblong elements, the tendon causes secure guiding of the electrode in the direction toward the muscle belly. In this way, the electrode may be "screwed forward" along the tendon in a simple and defined way and "screwed on and/or in" the muscle belly without special instruments. The tendon is used as a slide rail, along which the coiled parts may be screwed into the muscle tissue.

For more secure fastening, the distal end of one or more oblong elements may also have one or more barbs, however, the danger of minimal traumatization existing therefrom.

The stapedius muscle electrode configuration according to the invention may advantageously ensure, with minimal traumatization, secure fastening and close contact of the electrode with the stapedius muscle tissue. In this configuration, it can pick up the action currents generated upon a contraction of the stapedius muscle and relay them via a suitable connection to an analysis unit. The elastic properties of both oblong elements are selected so that the forces exerted thereby on the muscle belly cause secure fixing against dislocation and rejection as a result of muscle movements and simultaneously prevent pressure necrosis or other traumatization. By reversed rotation of the coiled sections around their center line, the electrodes may additionally be removed again essentially atraumatically. In addition, a large electrical contact area between electrode and tissue is achieved by the coiled implementation.

In a preferred embodiment, the distal end of one of the two oblong elements or preferably of both oblong elements is implemented as a cutting tip. In this way, a simple and essentially atraumatic insertion of the coiled part of the oblong element into the muscle tissue is possible.

In a preferred embodiment, the coiled parts of the two oblong elements are implemented in such a way that they may be pushed onto the area of the muscle belly adjoining the tendon upon the spiraling movement in the direction toward the muscle belly and radially expand and press elastically against the muscle belly. This may be achieved by suitable selection of the elastic properties of the two oblong elements. In the fastened state, a forward area of the coiled part of the two oblong elements runs on the surface of the area of the muscle belly adjoining the tendon and presses and elastically against it. The elastic properties of the two oblong elements are selected so that the forces exerted by them on the muscle belly cause secure fixing against dislocation and rejection as a result of muscle movements and simultaneously prevent pressure necrosis or other traumatization. Furthermore, it is especially preferable if this embodiment is combined with the implementation described above of the distal end of one or both oblong elements as a cutting tip. With the aid of the cutting tip or the cutting tips, the electrode may, when the coiled part of the two oblong elements are pushed onto the muscle belly, cut partially into the surface thereof, in order to implement a depression therein, which improves the fixing. Because only the surface of the muscle belly is affected, no practically relevant traumatization is connected to the use of the cutting tip.

In an advantageous embodiment, the coiled parts of the two oblong elements are situated interleaved in one another so that at least one turn of the coiled part of the other oblong element is situated between each two adjacent turns of the coiled part of one of the two oblong elements. The two coiled parts may have the same or different pitch and/or number of turns per unit of length. In the latter case, at least one turn of the first oblong element is not located between each two adjacent turns of the other oblong element. However, it is preferable for the coiled parts of the two oblong elements to be situated interleaved in one another so that the pitch is equal or approximately equal and precisely one turn of the coiled part of the other oblong element is situated between each two adjacent turns of the coiled part of each of the two oblong elements, so that the two coiled parts are situated in the form of a double helix. In other words, the two coiled parts represent two single helices running around one another and display a course which is comparable to a double-threaded screw. The individual turns of the two coiled parts alternate along the center line.

It is preferable for the two oblong elements or at least the coiled parts of the two oblong elements to have an identical shape and identical dimensions or an essentially identical shape and essentially identical dimensions.

In a preferred embodiment, the distal ends of the two oblong elements are situated directly adjacent to one another and together form the distal end of the electrode. In general, the distal end of one of the two oblong elements is situated along the center line at a slight distance behind the distal end of the other oblong element. If the two oblong elements or their coiled parts have an identical shape and identical dimensions, each coiled part follows the course of the other coiled part with an offset and the course of the part of the electrode formed by the two coiled parts corresponds to the course of the two coiled parts. In the case of identical oblong elements, the electrode has the same course and the same length as the two oblong elements.

It is preferable for the coiled parts of the two oblong elements to have the same coil diameter at every position along the shared center line. This diameter may be constant along the center line or change sectionally or continuously along the center line. However, the diameter locally corresponds at every point along the center line. In this way, it is advantageously ensured that none of the coiled parts of the two oblong elements projects into or protrudes from the volume enclosed by the coiled part of the other oblong element. Rather, the two coiled parts enclose a shared volume having "smooth" surface.

It is preferable for the coiled parts of the two oblong elements to be offset to one another along the shared center line by less than one turn length of at least one of the two coiled parts.

It is preferable for the two oblong elements to have a diameter of 20 to 300 μm, and more preferably of 50 to 180 μm. Through the selection of such a diameter, secure fastening may be connected with no or at most minimal traumatization. For a noncircular cross-section, the range specified above denotes the range in which both the maximum and also the minimum diameters lie. The two oblong elements may have identical or different diameters.

The cross-section of the two oblong elements or at least their coiled part may be circular, semicircular, oval, square, square having rounded corners, rectangular, rectangular having rounded corners, or in the form of an annular section. The mechanical properties of the oblong elements may be intentionally influenced by a suitable cross-section selection and achieve different axial bending rigidities in relation to bending in various directions, for example. The cross-section is preferably identical for the two oblong elements, but may also be different.

It is preferable for the two oblong elements to have an axial bending rigidity of 5 to 60 N mm$^2$, more preferably 5 to 50 N mm$^2$, and most preferably approximately 30 N mm$^2$. These values may be identical or different for the two oblong elements. It may be advantageous if at least one of the two oblong elements is designed so that the axial bending rigidity decreases from the proximal end of this oblong element to the distal end of this oblong element, e.g., from 60 N mm$^2$ at the proximal end to 25 N mm$^2$ at the distal end. In this way, the corresponding coiled part initially does not exert strong forces on the muscle belly upon reaching it and may be easily expanded and pushed onto the muscle belly, for example. In the further course of the fastening procedures, sections of the coiled part of the particular oblong element reach the muscle belly, which exert greater forces and ensure secure fastening. These sections are guided by the more distal sections which are already connected to the muscle belly.

Furthermore, it is preferable for the coiled parts of the two oblong elements to have a cross-sectional diameter of 80 to 800 μm and more preferably of 100 to 500 μm. These cross-sectional diameters relate to the diameter of a cross-sectional area of the volume enclosed and/or defined by the coiled section perpendicular to the extension direction of this volume and/or of the coiled part. For a noncircular cross-section, the range specified above denotes the range in which both the maximum and also the minimum diameters lie. The cross-sectional diameters may be identical or different for the two oblong elements.

It is preferable for the coiled parts of the two oblong elements to have a length of 0.1 to 3 mm and more preferably of 0.5 to 1.5 mm in their extension direction. This length may be identical or also different for the two oblong elements.

Furthermore, it is preferable for the number of turns of the coiled parts of the two oblong elements to be ¼ to six and more preferably ¼ to 1. The number of turns typically specifies how often the coiled part completely circles its center line. A low turn number has the advantage that "threading" on the tendon only requires a few revolutions of the electrode configuration, so that difficulties with twisting of the lines are avoided. The two oblong elements may have identical or also different numbers of turns.

It is preferable for the two oblong elements to have stainless steel, in particular surgical stainless steel 316L (X5CrNiMo18.10), a CrCoMo alloy, a NiTi alloy, in particular a NiTi memory alloy, platinum, a PtIr alloy, silver, gold, palladium, tantalum, or titanium or an alloy thereof. The material composition of the two oblong elements is preferably identical, but may also be different.

Furthermore, it is preferable for the two oblong elements or one of them to be at least partially coated with silicon carbide, pyrolytic carbon, and/or diamond-like carbon. The effective electrode area may be increased by such a coating. A fractal coating is particularly advantageous. An increase of the active surface may alternatively or additionally also be achieved by implementing axial longitudinal grooves in one or both oblong elements. Such a design also has the advantage of secure fastening of the electrode.

It may also be advantageous if the two oblong elements or at least one of them is provided with insulation along a part of its length, which preferably comprises a hydrolysis-stabilized silicone elastomer, polyether, or polyether urethane elastomer. This insulation may be provided, for example, in a non-coiled part of the oblong elements and/or in a proximal area of the coiled parts. In the case of insulation, the non-insulated area of the oblong elements forms the actual electrode. This non-insulated area must itself correspondingly be coiled as specified above at least along a part of its length.

In a preferred embodiment each of the two oblong elements has a wire or is preferably a wire.

Furthermore, it is preferable for each of the two oblong elements to be connected to an electrical line for deriving the action currents picked up by the electrode. These lines are preferably implemented as thinner than the particular oblong element and as thin as possible overall, in order to give as little resistance as possible to the handling of the electrode configuration during the fastening on the stapedius muscle.

The electrodes may not only be implemented having two oblong elements as the bipolar electrode for bipolar derivations. It is also possible to provide still more oblong elements, in order to form a multipolar electrode.

The stapedius muscle electrode configuration described above is, in a preferred embodiment, part of a system which, in addition to the stapedius muscle electrode configuration, has an oblong insertion instrument for inserting the stapedius muscle electrode configuration into a human body and for fastening the stapedius muscle electrode on a human stapedius muscle. The proximal end of at least one of the two oblong elements (or, in multipolar electrodes, possibly the further oblong elements) is detachably connected to a tip of the insertion instrument. The connection is designed so that the insertion element may be detached from the electrode configuration by pulling and/or rotating the insertion instrument after fastening the electrode on the stapedius muscle. In an especially preferred embodiment, the mechanical connection between the tip of the insertion instrument and the proximal end(s) of the oblong elements is provided with a weakened zone, which provides an intended breakpoint. The insertion instrument may thus be separated from the electrode configuration in a defined way with atraumatic force application.

BRIEF DESCRIPTION OF THE DRAWINGS

The invention is explained in greater detail hereafter on the basis of exemplary embodiments with reference to the drawings.

DETAILED DESCRIPTION OF THE INVENTION

Figure 1:
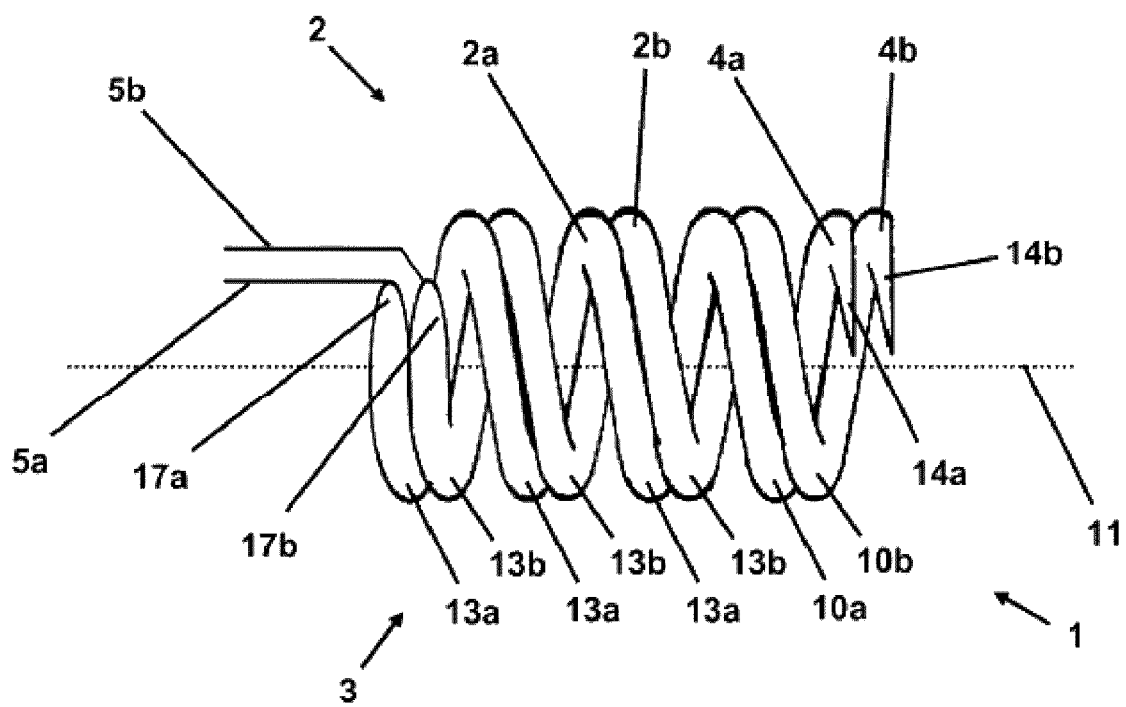
FIG. 1 shows a schematic view of a stapedius muscle electrode configuration according to the invention.

The stapedius muscle electrode configuration 1 shown in FIG. 1 contains a bipolar electrode 2, which has a first flexible elastic wire 2a made of an electrically conductive and biocompatible material and a second flexible elastic wire 2b made of an electrically conductive and biocompatible material. Each of the two wires 2a, 2b is pre-shaped as coiled along its entire length, and the two wires 2a, 2b have an identical shape and identical dimensions. They are interleaved in one another in such a way that they circle a shared center line 11 and enclose a shared volume, and run offset a fraction of one turn length from one another along the center line 11, so that together they form a double helix. The wire 2b is fastened along its entire length to the right side of the wire 2a in FIG. 1, the two wires 2a, 2b being electrically insulated from one another by insulation (not shown). The fastening of the two wires 2a, 2b to one another is preferably caused by a suitable insulating material, such as a plastic layer provided between the two wires 2a, 2b. Except for the insulation between the wires 2a, 2b, the wires 2a, 2b are uninsulated, so that they may be brought into electrical contact with a stapedius muscle along their entire length. It is obvious from FIG. 1 that the two wires 2a, 2b may be viewed together as a single, coiled pre-shaped oblong element, whose general course corresponds to the course of the two wires 2a, 2b. Therefore, the electrode 2 is itself a coiled oblong element, whose course corresponds to the course of the two individual wires 2a, 2b.

Each wire 2a, 2b is connected at its proximal end 17a or 17b to an electrical line 5a or 5b, respectively, which is used as an electrical connection between the particular wire 2a or 2b and a suitable analysis unit (not shown). Alternatively, instead of separate lines 5a, 5b, wires 2a, 2b may also be provided, which have a distal section or part 3, in which the particular wire 2a or 2b is pre-shaped coiled, and which extends up to the distal end 4a or 4b of the wire 2a or 2b, and a proximal, non-coiled section 5a or 5b, which is used as the electrical connection between the coiled section 3 and a suitable analysis unit (not shown). Mixed forms are also possible, i.e., one wire may be completely coiled and connected to a separate line, while the other wire has a proximal, non-coiled section usable as an electrical connection, or one or both wires may have a non-coiled proximal section, which is connected at its proximal end to a separate electrical line.

Figure 2:
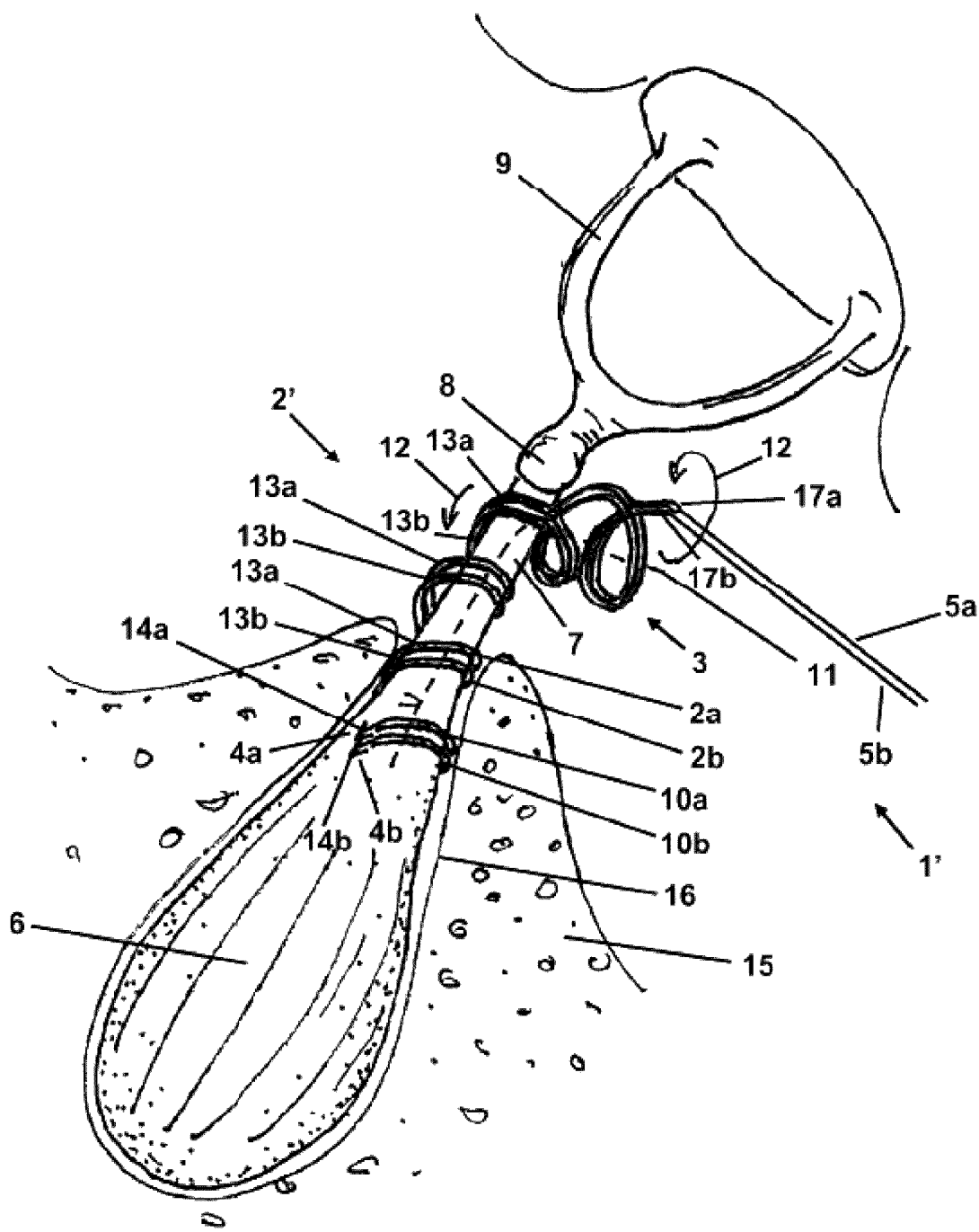
FIG. 2 shows a schematic sectional view of a part of the middle ear having a stapedius muscle electrode configuration according to the invention, whose electrode is fastened on the stapedius muscle.

On its distal ends 4a, 4b, each wire 2a, 2b is provided with a cutting tip 14a, 14b, with the aid of which the electrode 2, as explained hereafter with reference to FIG. 2, may cut into the surface of a stapedius muscle, in order to improve the hold of the electrode 2 on the stapedius muscle.

It is obvious from FIG. 1 that each wire 2a, 2b and thus the entire double-helix-shaped electrode 2 has four turns. The frontmost turn is identified by the reference numerals 10a, 10b in FIG. 1, while the remaining turns are identified by the reference numerals 13a, 13b.

In FIG. 2, a stapedius muscle electrode configuration 1' is shown during the procedure of fastening the electrode 2' on the belly 6 of a stapedius muscle. The stapedius muscle electrode configuration 1' is identical to the stapedius muscle electrode configuration 1 shown in FIG. 1 except for the difference that its electrode 2' has five turns 10a, 10b, 13a, 13b, while the electrode 2 from FIG. 1 has only four turns 10a, 10b, 13a, 13b. For reasons of visibility, the two wires 2a, 2b of the electrode 2' are shown at a certain distance to one another without a recognizable fastener between the wires 2a, 2b. Of course, the wires 2a, 2b are either connected to one another along their entire length by an insulating material layer situated between them, as in the embodiment of FIG. 1, or by individual fasteners which are spaced apart from one another.

As is obvious from FIG. 2, the belly 6 of the stapedius muscle is connected via a tendon 7 to the head 8 of the stirrup 9. For the implantation of the stapedius muscle electrode 2', firstly its frontmost turn 10a, 10b is laid around the tendon 7 (and/or the two wires 2a, 2b have their frontmost turns 10a and 10b, respectively, laid around the tendon 7 simultaneously). Subsequently, the wires 2a, 2b (together with the lines 5a, 5b) and/or the electrode 2' are rotated as a unit around the center line 11, as indicated by the arrows 12. Due to the coiled implementation of the wires 2a, 2b and therefore of the electrode 2', they are thus advanced in a spiral along the tendon 7 in the direction toward the muscle belly 6, with each revolution, a further turn 13a, 13b of the wires 2a, 2b and thus of the electrode 2' "threading" onto the tendon 7 and the electrode 2' being moved by one turn distance along the tendon in the direction toward the stapedius muscle. As may be inferred from FIG. 2, the radial cross-sectional diameter of the turns 10a, 10b, 13a, 13b is selected so that the turns 10a, 10b, 13a, 13b enclose the tendon 7 with some play.

After some time, the front end 4a, 4b of the electrode 2' reaches the muscle belly 6. The rotation is then continued in order to push or more or less "screw" a number of the turns 13a, 13b (only three of which are identified by reference numerals in FIG. 2) onto the area of the muscle belly 6 adjoining the tendon 7. The radial diameter of the coiled wires 2a, 2b is selected so that they have to radially expand when they are pushed on. Because of the elastic implementation, the wires 2a, 2b and thus the electrode 2' press against the surface of the muscle belly 6 and are thus fixed thereon. By reversed rotation of the stapedius muscle electrode 2', it may be detached and removed from the muscle belly 6 and from the tendon 7. The fixation is additionally improved by the cutting tips 14a, 14b provided on the distal ends 4a, 4b of the wires 2a, 2b, which each cut a flat depression (not shown) into the surface of the muscle belly 6, into which the particular wire 2a or 2b runs.

The stapedius muscle electrode 2, 2' may be fastened easily on the channel 16 implemented in the bone 15, without the bony structure 15 having to be changed. Even if the cutting tips 14a, 14b are used, practically no relevant traumatization of the muscle belly 6 occurs.

Figure 3:
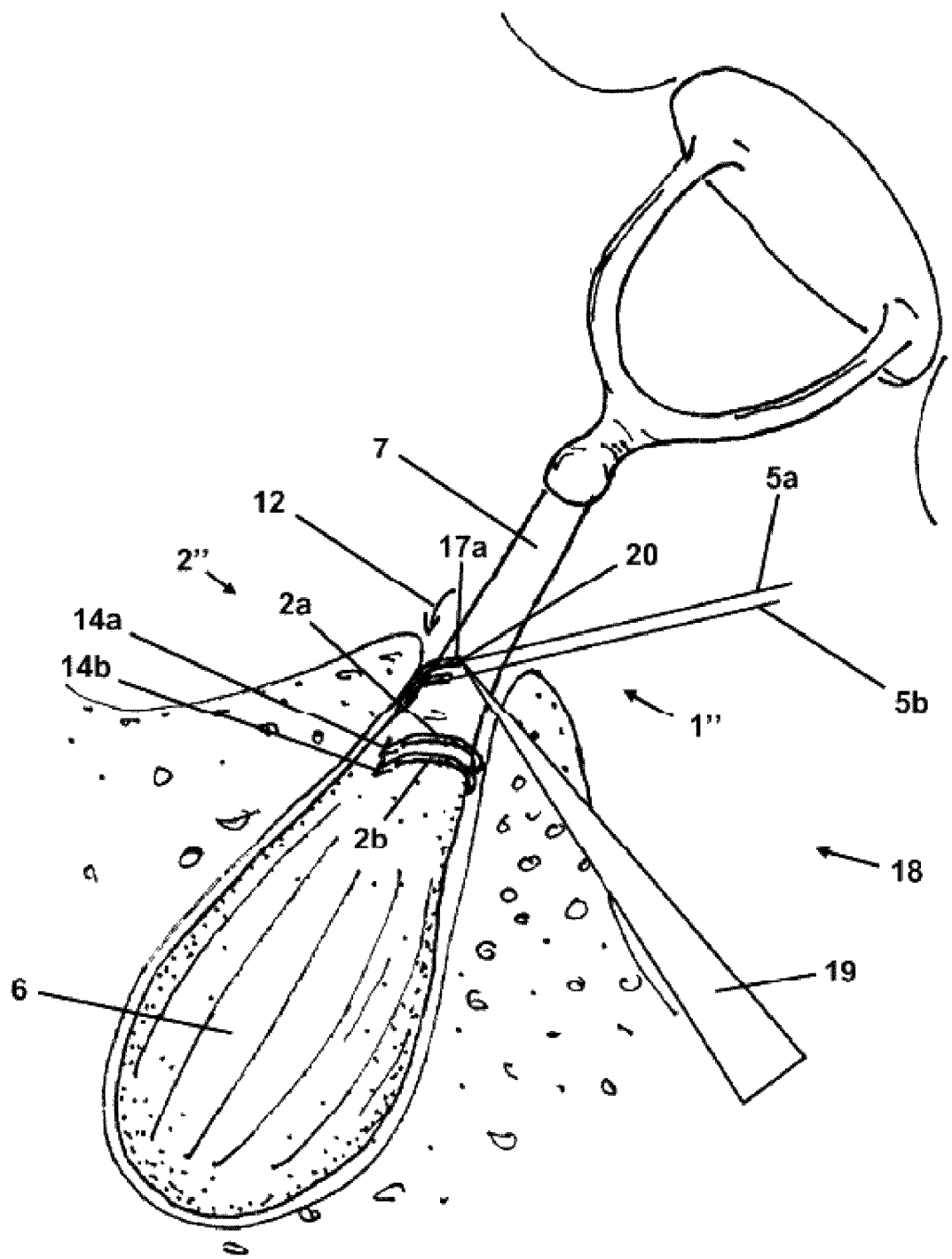
FIG. 3 shows a schematic sectional view of a part of the middle ear having a stapedius muscle electrode configuration according to the invention, which is connected to an insertion instrument, and whose electrode is fastened on the stapedius muscle.

FIG. 3 shows a further stapedius muscle electrode configuration 1", which differs from the stapedius muscle electrode configurations 1 and 1' shown in FIGS. 1 and 2 primarily in that its electrode 2" and/or the two wires 2a, 2b of the electrode 2" only have one complete turn 10a, 10b and thus more or less only a terminal turn. It is to be noted that the electrode 2" may also be implemented so that it and its wires 2a, 2b have less than one complete turn 10a, 10b. Furthermore, the stapedius muscle electrode configuration 1" is part of a system 18 which, in addition to the stapedius muscle electrode configuration 1", also has an oblong insertion instrument 19. This instrument has a tip which is mechanically connected to the proximal end 17a of the wire 2a. This connection is provided with a weakened zone 20, which leads to an intended breakpoint, so that the insertion instrument 19 may be detached from the electrode configuration 1" by pulling and/or rotating in a defined way after the electrode 2" is fastened on the muscle belly 6 in a simple way and without the danger of traumatization of the muscle belly 6 or detachment of the electrode 2" from the muscle belly 6. It is also possible that the oblong insertion element 19 is not only connected to the proximal end of one of the two wires 2a, 2b, but rather to the proximal ends 17a, 17b of both wires 2a, 2b.

The invention claimed is:

1. A stapedius muscle electrode configuration for the detection of the action currents generated upon a contraction of a human stapedius muscle comprising:
    an electrode adapted for bipolar derivation for fastening on a human stapedius muscle, the electrode including two flexible elastic electrically-conductive oblong elements each having a distal end and a proximal end,
    wherein at least a portion of the electrode towards the distal end is pre-shaped in a coil so that:
        i. the distal end and an adjoining section of oblong element is adapted to be laid at least partially around a tendon running between the stapedius muscle and a stirrup ossicle, and
        ii. the coil shaped portion of the electrode may be moved along the tendon while guided in the direction toward the stapedius muscle and at least partially screwed into an area of muscle belly of the stapedius muscle adjoining the tendon and/or pushed onto this area, and
    wherein the oblong elements are electrically insulated and their coiled portions are interleaved so that the oblong elements circle a shared center line and are adapted to be laid around the tendon, guided along the tendon, and brought into contact with the stapedius muscle together.

2. A stapedius muscle electrode configuration according to claim 1, wherein the distal end of at least one of the oblong elements includes cutting tip.

3. A stapedius muscle electrode configuration according to claim 1, wherein the coiled portions are adapted to be pushed onto the muscle belly adjoining the tendon and to expand radially and press elastically against the muscle belly.

4. A stapedius muscle electrode configuration according to claim 1, wherein the coiled portions are interleaved so that at least one turn of the one oblong element is situated between adjacent turns of the other oblong element.

5. A stapedius muscle electrode configuration according to claim 4, wherein the coiled portions are interleaved so that one turn of one of the oblong elements is situated between two adjacent turns of the other oblong element so that the two coiled parts form a double helix shape.

6. A stapedius muscle electrode configuration according to claim 1, wherein the two oblong elements have the same shape and dimensions.

7. A stapedius muscle electrode configuration according to claim 1, wherein the distal ends of the oblong elements are situated directly adjacent to one another and together form the distal end of the electrode.

8. A stapedius muscle electrode configuration according to claim 1, wherein the coiled portions have the same coil diameter at every position along the shared center line.

9. A stapedius muscle electrode configuration according to claim 1, wherein the coiled portions are offset along the shared center line by less than one turn distance of at least one of the two coiled portions.

10. A stapedius muscle electrode configuration according to claim 1, wherein the oblong elements have a diameter of 20 to 300 µm.

11. A stapedius muscle electrode configuration according to claim 10, wherein the oblong elements have a diameter of 50 to 180 µm.

12. A stapedius muscle electrode configuration according to claim 1, wherein the oblong elements have a cross-section that is circular, semicircular, oval, square, square with rounded corners, rectangular, or rectangular with rounded corners.

13. A stapedius muscle electrode configuration according to claim 1, wherein the oblong elements have an axial bending rigidity of 5 to 60 N/mm$^2$.

14. A stapedius muscle electrode configuration according to claim 13, wherein at least one of the oblong elements is adapted so that the axial bending rigidity decreases from the proximal end to the distal end.

15. A stapedius muscle electrode configuration according to claim 1, wherein the coiled portions have a cross-sectional diameter of 80 to 800 µm.

16. A stapedius muscle electrode configuration according to claim 1, wherein the coiled portions have a length of 0.1 to 3 mm in their extension direction.

17. A stapedius muscle electrode configuration according to claim 1, wherein the coiled portions have ¼ to 6 coiled turns.

18. A stapedius muscle electrode configuration according to claim 1, wherein the oblong elements are made of stainless steel, a CrCoMo alloy, a NiTi alloy, platinum, a PtIr alloy, silver, gold, palladium, tantalum, or titanium, or an alloy thereof.

19. A stapedius muscle electrode configuration according to claim 1, wherein the oblong elements are at least partially coated with at least one of silicon carbide, pyrolytic carbon, or diamond-like carbon.

20. A stapedius muscle electrode configuration according to claim 19, wherein the coating is implemented as a fractal material.

21. A stapedius muscle electrode configuration according to claim 1, wherein the oblong elements are at least partially provided with polyurethane or silicone elastomer insulation.

22. A stapedius muscle electrode configuration according to claim 1, wherein the oblong elements are each formed by a wire.

23. A stapedius muscle electrode configuration according to claim 1, wherein each of the oblong elements is connected to an electrical wire to derive action currents.

24. A stapedius muscle electrode configuration according to claim 1, further comprising:
    an oblong insertion instrument adapted for inserting the stapedius muscle electrode configuration into a human body and for fastening the stapedius muscle electrode on a human stapedius muscle, wherein the proximal end of at least one of the oblong elements is detachably connected to a tip of the insertion instrument.

25. A stapedius muscle electrode configuration according to claim 24, wherein the connection between the tip of the insertion element and the proximal ends of the oblong elements has a weakened zone which provides an intended breakpoint.

* * * * *